(12) United States Patent
Arvanitidou et al.

(10) Patent No.: US 6,534,472 B1
(45) Date of Patent: Mar. 18, 2003

(54) ANTIBACTERIAL CLEANING WIPE

(75) Inventors: Evangelia Arvanitidou, Kendall Park, NJ (US); Karen Wisniewski, Bound Brook, NJ (US); Barbara Thomas, Princeton, NJ (US); Bruce Nascimbeni, Millstone, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/159,554

(22) Filed: May 31, 2002

Related U.S. Application Data

(63) Continuation-in-part of application No. 10/086,165, filed on Feb. 27, 2002, now Pat. No. 6,432,904, which is a continuation-in-part of application No. 10/008,715, filed on Nov. 13, 2001, now Pat. No. 6,446,925.

(51) Int. Cl.[7] ............................................. C11D 17/00

(52) U.S. Cl. ..................... 510/438; 510/295; 510/499; 510/501; 510/503; 510/505; 510/424; 510/428; 134/42; 428/288; 15/209.1

(58) Field of Search ................................. 510/438, 424, 510/428, 499, 295, 501, 503, 505; 134/42; 428/288; 15/209.1

(56) References Cited

U.S. PATENT DOCUMENTS

| | | | | | |
|---|---|---|---|---|---|
| 4,725,489 A | * | 2/1988 | Jones et al. | .................. | 428/289 |
| 5,141,803 A | * | 8/1992 | Pregozen | .................... | 428/288 |
| 6,284,259 B1 | * | 9/2001 | Beerse et al. | ................ | 424/404 |
| 6,340,663 B1 | * | 1/2002 | Deleo et al. | ................ | 510/438 |

* cited by examiner

*Primary Examiner*—Necholus Ogden
(74) *Attorney, Agent, or Firm*—Richard E. Nanfeldt

(57) ABSTRACT

An antibacterial dishwashing cleaning wipe comprising a single layer needle punched fabric wherein the fabric is impregnated with an antibacterial cleaning composition.

7 Claims, No Drawings

ANTIBACTERIAL CLEANING WIPE

RELATED APPLICATION

This application is a continuation in part application of U.S. Ser. No. 10/086,165 filed Feb. 27, 2002 was U.S. Pat No. 6,432,904 which in turn is a continuation in part application of U.S. Ser. No. 10/008,715 filed Nov. 13, 2001 now U.S. Pat. No. 6,446,925.

FIELD OF INVENTION

The present invention relates to an antibacterial dishwashing cleaning wipe which is single or multi layer fabric substrate which has been impregnated with a liquid cleaning composition.

BACKGROUND OF THE INVENTION

The patent literature describes numerous wipes for both body cleaning and cleaning of hard surfaces but none describe wipes for cleaning dishware flatware, pots and pans. U.S. Pat. Nos. 5,980,931, 6,063,397and 6,074,655 teach a substantially dry disposable personal cleansing product useful for both cleansing and conditioning the skin and hair. U.S. Pat. No. 6,060,149 teaches a disposable wiping article having a substrate comprising multiple layers.

U.S. Pat. Nos. 5,756,612; 5,763,332; 5,908,707; 5,914,177; 5,980,922 and 6,168,852 teach cleaning compositions which are inverse emulsions.

U.S. Pat. Nos. 6,183,315 and 6,183,763 teach cleaning compositions containing a proton donating agent and having an acidic pH. U.S. Pat. Nos. 5,863,663; 5,952,043; 6,063,746 and 6,121,165 teaches cleaning compositions which are oil in water emulsions.

SUMMARY OF THE INVENTION

A single use cleaning wipe for dishwashing application comprises a water insoluble substrate, impregnated with an antibacterial cleaning composition containing at least 20 wt. % of a mixture of at least three anionic surfactants, a proton donating agent, a zwitterionic surfactant, polyethylene glycol and water.

The liquid antibacterial cleaning compositions of this invention are not an emulsion and do not contain an ethoxylated nonionic surfactant, potassium sorbate, a polysaccharide polymer, a polycarboxylate polymer, polyvinyl alcohol polymer, polyvinylpyrrolidone polymer, methyl vinyl ether polymer or a glucoside surfactant

DETAILED DESCRIPTION OF THE INVENTION

The present invention relates to a cleaning wipe for dishware, flatware, pots and pans which comprises approximately:

(a) 20 wt. % to 95 wt. % of a water insoluble substrate; and
(b) 5 wt. % to 80 wt. % of a liquid antibacterial cleaning composition being impregnated in said water insoluble substrate, wherein said liquid cleaning composition comprises:
  (i) 7 wt. % to 16 wt. % of an alkali metal salt of an anionic sulfonated surfactant;
  (ii) 6 wt. % to 15 wt. % of an alkali metal salt or ammonium salt of an ethoxylated alkyl ether sulfate anionic surfactant;
  (iii) 0.1 wt. % to 4 wt. % of a zwitterionic surfactant;
  (iv) 7 wt. % to 16 wt. % of an alkaline earth metal salt of a sulfonated anionic surfactant;
  (v) 0.5 wt. % to 8 wt. % of a polyethylene glycol;
  (vi) 0.1% to 4 wt. % of a proton donating agent; and
  (vii) the balance being water, wherein the composition does not contain an ethoxylated nonionic surfactant, potassium sorbate, a polysaccharide polymer, a polycarboxylate polymer, polyvinyl alcohol polymer, polyvinylpyrrolidone polymer, polyethylene glycol polymer, methyl vinyl ether polymer or glucoside surfactant and the antibacterial cleaning composition has a Gram Positive Residual Effective Index as measured by the method set forth in U.S. Pat. 6,284,259 of less than 0.35, preferably less than 0.3.

Suitable water-soluble non-soap, anionic surfactants used in the instant compositions include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, ammonium, magnesium and mono-, di- or tri-$C_2$–$C_3$ alkanolammonium, with the sodium, magnesium and ammonium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is a mixture of an alkali metal ammonium salt and an alkaline earth metal salt of a linear alkyl benzene sulfonate having a high content of 3-(or higher) phenyl isomers and a correspondingly low content (well below 50%) of 2-(or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an α-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735,096.

Examples of satisfactory anionic sulfate surfactants are the alkali metal or ammonium salt $C_8$–$C_{18}$ alkyl sulfate salts the ethoxylated $C_8$–$C_{18}$ alkyl ether sulfate salts having the formula $R(OC_2H_4)n\ OSO_3M$ wherein n is 1 to 12, preferably 1 to 5, and M is a metal cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the ethoxylated alkyl ether sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. The ethoxylated alkyl ether sulfates differ from one another in the number of moles of ethylene oxide reacted with one mole of alkanol. Preferred alkyl sulfates and preferred ethoxylated alkyl ether sulfates contain 10 to 16 carbon atoms in the alkyl group.

The ethoxylated $C_8$–$C_{12}$ alkylphenyl ether sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic surfactants are the $C_9$–$C_{15}$ alkyl ether polyethenoxyl carboxylates having the structural formula $R(OC_2H_4)nOX\ COOH$ wherein n is a number from 4 to 12, preferably 5 to 10 and X is selected from the group consisting of

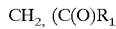

and

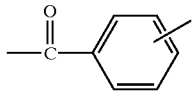

wherein $R_1$ is a $C_1$–$C_3$ alkylene group. Preferred compounds include $C_9$–$C_{11}$ alkyl ether polyethenoxy (7–9) C(O) $CH_2CH_2COOH$, $C_{13}$–$C_{15}$ alkyl ether polyethenoxy (7–9)

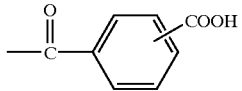

and $C_{10}$–$C_{12}$ alkyl ether polyethenoxy (5–7) CH2COOH. These compounds may be prepared by condensing ethylene oxide with appropriate alkanol and reacting this reaction product with chloracetic acid to make the ether carboxylic acids as shown in U.S. Pat. No. 3,741,911 or with succinic anhydride or phthalic anhydride. Obviously, these anionic surfactants will be present either in acid form or salt form depending upon the pH of the final composition, with salt forming cation being the same as for the other anionic surfactants.

The polyethylene glycol is depicted by the formula:

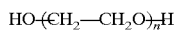

wherein n is about 8 to about 225, more preferably about 10 to about 100,000, wherein the polyethylene glycol has a molecular weight of about 200 to about 1,000. One preferred polyethylene glycerol is PEG1000 which is a polyethylene glycol having a molecular weight of about 1000.

The proton donating agent is selected from the group consisting of inorganic acids such as sulfuric acid and hydrochloric acid and hydroxy containing organic acid, preferably a hydroxy aliphatic acid, wherein the hydroxy contains organic acid is selected from the group consisting of lactic acid or citric acid, orthohydroxy benzoic acid or glycolic acid and mixtures thereof.

The water-soluble zwitterionic surfactant (betaine), which is used in the instant cleaning composition and provides good foaming properties and mildness to the composition. The zwitterionic surfactant is a water soluble betaine having the general formula:

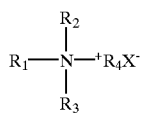

wherein $X^-$ is selected from the group consisting of $SO_3^-$ and $CO_2^-$ and $R_1$ is an alkyl group having 10 to about 20 carbon atoms, preferably 12 to 16 carbon atoms, or the amido radical:

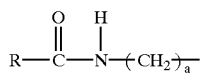

wherein R is an alkyl group having about 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia) acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine.

The water is present in the composition at a concentration of about 5 wt. % to 70 wt. %.

The cleaning composition of this invention may, if desired, also contain other components either to provide additional effect or to make the product more attractive to the consumer. The following are mentioned by way of example: Antibacterial agents such as 2,4,4'-trichloro-2'hydroxydiphenyl ether colors or dyes in amounts up to 0.5% by weight; pH adjusting agents, such as sulfuric acid or sodium hydroxide, can be used as needed.

Preservatives which can be used in the instant compositions at a concentration of 0.005 wt. % to 3 wt. %, more preferably 0.01 wt. % to 2.5 wt. % are: benzalkonium chloride; benzethonium chloride,5-bromo-5-nitro-1, 3dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N'-(hydroxy methyl) urea; 1-3-dimethyol-5,5-dimethyl hydantoin; formaldehyde; iodopropynl butyl carbamata, butyl paraben; ethyl paraben; methyl paraben; propyl paraben, mixture of methyl isothiazolinone/ methyl-chloroisothiazoline in a 1:3 wt. ratio; mixture of phenoxythanol/butyl paraben/methyl paraben/propylparaben; 2-phenoxyethanol; trishydroxyethyl-hexahydrotriazine; methylisothiazolinone; 5-chloro-2-methyl-4-isothiazolin-3-one; 1,2-dibromo-2,4-dicyanobutane; 1-(3-chloroalkyl)-3,5,7-triaza-azoniaadamantane chloride; and sodium benzoate. PH adjusting agents such as sulfuric acid or sodium hydroxide can be used as needed.

The product of the present invention comprises a water insoluable substrate with one or more layers. Each layer may have different textures and abrasiveness. Differing textures can result from the use of different combinations of materials or from the use of different manufacturing processes or a combination thereof. A dual texture substrate can be made to provide the advantage of a more abrasive side for cleaning difficult to remove soils. A softer side can be used for fine dishware and flatware. The substrate should not dissolve or break apart in water. It is the vehicle for delivering the cleaning composition to dishware, flatware, pots and pans. Use of the substrate enhances lathering, cleaning and grease removal.

A wide variety of materials can be used as the substrate. It should have sufficient wet strength, abrasivity, loft and porosity. Examples include, non woven substrates, wovens substrates, hydroentangled substrates and sponges.

Examples of suitable non woven water insoluable substrates include, 100% cellulose Wadding Grade 1804 from Little Rapids Corporation, 100% polypropylene needlepunch material NB 701-2.8-W/R from American Non-wovens Corporation, a blend of cellulosic and synthetic fibres-Hydraspun 8579 from Ahistrom Fibre Composites, and &0% Viscose/30% PES Code 9881 from PGI Nonwovens Polymer Corp.

Another useful substrate is manufactured by Jacob Holm-Lidro Rough. It is a composition material comprising a 65/35 viscose rayon/polyester hydroentangled spunlace layer with a hydroenlongated bonded polyeser scribbly layer.

Still another useful substrate is manufactured by Texel. It is a composite material manufactured from a layer of coarse fiber 100% polypropylene needlepunch, an absorbent cellulose core and a fine fiber polyester layer needlepunched together. The polypropylene layer can range from 1.5 to 3.5 oz/sq. yd. The cellulose core is a creped paper layer ranging from 0.5 to 2 oz./sq. yd. The fine fiber polyester layer can range from 0.5 to 2 oz./sq. yd.

The product of the present invention comprising multiple layers may be ultrasonically bonded after applying the coating of one or more of the layers. Alternatively layers may be bonded together by needlepunch, thermal bonding, chemical bonding, or sonic bonding prior to applying the coating.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following composition (in wt. %) was prepared by simple batch mixing at room temperature. The cleaning wipe was made by the previously described impregnation process.

|  | A | | |
|---|---|---|---|
| Part I | | | |
| Ammonium ethoxylated alkyl ether sulfate | 15.34 | | |
| Magnesium linear alkyl benzene sulfonate | 26.6 | | |
| Lauryl polyglucoside | 3.3 | | |
| Lauramide myristamide monoethanol amide | 3.5 | | |
| Sodium xylene sulfonate | 4.0 | | |
| Ethanol | 1.8 | | |
| Sodium bisulfate | 0.2 | | |
| HEDTA | 0.67 | | |
| Preservative | 0.47 | | |
| Water | Bal. | | |
| Part 1 Formula A | 1 | 3 | |
| NB-701-2.8/WR fabric | 1 | | |
| Wadding Grade 1804 | | 1 | |
| SRF #8265C | | | 1 |
| SRF 1262 | | | 1 |

While particular embodiments of the invention and the best mode contemplated by the inventors for carrying out the invention have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

EXAMPLE 2

The following composition (in wt. %) was prepared by simple batch mixing at room temperature. The cleaning wipes were made by the previously described impregnation process.

|  | A | | |
|---|---|---|---|
| Sodium LAS | 3.52 | | |
| Magnesium LAS | 8.48 | | |
| Ammonium Ether Sulfate (1.3 EO) | 11.50 | | |
| APG | 10.0 | | |
| Lauramide myristamido propyl amine oxide | 5.42 | | |
| Sodium xylene sulfonate | 1.50 | | |
| Ethanol | 6.20 | | |
| Penta sodium pentatate | 0.125 | | |
| Preservative (Dowicil 75) | 0.07 | | |
| Fragrance | 0.45 | | |
| Water | Bal. | | |
| Part 1 Formula A | 62 | 53 | 64 |
| NB-701-2.8/WR fabric | 38 | | |
| Texel | | 47 | |
| Jacob Holm-Lidro Rough | | | 36 |

The following composition (in wt. %) was prepared by simple batch mixing at room temperature. The cleaning wipe was made by the previously described impregnation process.

|  | Wt. % |
|---|---|
| Mg LAS | 12.915 |
| Na LAS | 12.915 |
| Ammonium Ether Sulfate (1.3 EO) | 12.67 |
| CAP betaine | 0.5 |
| Lactic acid | 2 |

-continued

| | Wt. % |
|---|---|
| PEG 300 | 4 |
| Fragrance | 0.45 |
| Water | Balance |

What is claimed:

1. A dishwashing cleaning wipe which comprises approximately:
 (a) 20 wt. % to 95 wt. % of a water insoluble substrate; and
 (b) 5 wt. % to 80 wt. % of antibacterial liquid cleaning composition being impregnated in said water insoluble substrate, wherein said liquid cleaning composition comprises:
  (i) 7 wt. % to 16 wt. % of an alkali metal or ammonium salt of an anionic sulfonate surfactant;
  (ii) 7 wt. % to 16 wt. % of an alkaline earth metal salt of an anionic sulfonate surfactant;
  (iii) 6% to 15% of an alkaline earth metal salt of an anionic sulfate surfactant;
  (iv) 0.1 wt. % to 4 wt. % of a zwitterionic surfactant;
  (v) 0.1 wt. % to 4 wt. % of a proton donating agent; and
  (vi) the balance being water wherein the composition does not contain an ethoxylated nonionic surfactant, potassium sorbate, a polysaccharide polymer, a polycarboxylate polymer, polyvinyl alcohol polymer, polyvinylpyrrolidone polymer, a polyethylene glycol polymer, methyl vinyl ether polymer or glucoside surfactant and the antibacterial cleaning composition has a Gram Positive Residual Effect Index of less than 0.3.

2. The wipe according to claim 1, wherein both of said sulfonate surfactant are a linear $C_{10}$–$C_{16}$ alkyl benzene sulfonate.

3. The wipe according to claim 1, wherein said sulfate surfactant is an ethoxylated $C_8$–$C_{18}$ alkyl ether sulfate.

4. The wipe according to claim 1, further including about 0.01 to about 1.5 wt. % of a perfume.

5. The wipe according to claim 1, wherein said water insoluble substrate comprises one or more materials selected from nonwoven substrates, woven substrates, hydroentangeld substrates and sponges.

6. The wipe according to claim 1, wherein said proton donating agent is selected from the group consisting of citric acid, lactic acid, glycolic acid and ortho-hydroxy benzoic acid and mixtures thereof.

7. A method of manufacturing a product according to claim 1, wherein the cleaning composition is added or impregnated into the water insoluble substrate by spraying, dipping, extrusion coating or slot coating.

* * * * *